United States Patent [19]

Kopolow et al.

[11] Patent Number: 5,221,531
[45] Date of Patent: Jun. 22, 1993

[54] POLYMER HAIR FIXATIVES, AQUEOUS-BASED SOLUTION PROCESS FOR MAKING SAME AND WATER-BASED HAIR SPRAY FORMULATIONS THEREWITH WHICH MEET VOC STANDARDS

[75] Inventors: Stephen L. Kopolow, Plainsboro, N.J.; Yoon T. Kwak, Brooklyn, N.Y.; Mohammed Tazi, Marietta, Ga.; Edward W. Walls, Jr., Cranford, N.J.

[73] Assignee: ISP Investments Inc., Wilmington, Del.

[21] Appl. No.: 796,998

[22] Filed: Nov. 25, 1991

[51] Int. Cl.$^5$ .............................................. A61K 7/11
[52] U.S. Cl. .............................. 424/71; 424/70; 424/78.24; 424/DIG. 2
[58] Field of Search ............... 424/71, 48, 47, DIG. 2, 424/DIG. 1, 78.24; 524/548

[56] References Cited

U.S. PATENT DOCUMENTS 4,521,404  6/1985  Lorenz et al. .................. 424/47
5,045,617  9/1991  Shih et al. ..................... 524/548

Primary Examiner—Thurman K. Page
Assistant Examiner—D. Colucci
Attorney, Agent, or Firm—Walter Katz; Marilyn J. Maue; Joshua J. Ward

[57] ABSTRACT

The present invention provides a polymer hair fixative comprising vinyl caprolactam, vinyl pyrrolidone, dimethylaminoethyl methacrylate and acrylate acid, in the form of sodium acrylate, an aqueous-based solution process for making such polymers, and water-based hair spray compositions including such polymer fixatives which meet VOC standards.

16 Claims, No Drawings

POLYMER HAIR FIXATIVES, AQUEOUS-BASED SOLUTION PROCESS FOR MAKING SAME AND WATER-BASED HAIR SPRAY FORMULATIONS THEREWITH WHICH MEET VOC STANDARDS

BACKGROUND OF THE INVENTION

1. Field of the Invention

This invention relates to polymeric hair fixatives, an aqueous-based solution process for making polymer fixatives, and to water-based hair spray formulations which meet VOC standards.

2. Description of the Prior Art

Recent legislation in California and other states have mandated that hair sprays and other products must have low volatile organic chemicals (VOC) in the composition. Many useful hair fixatives, however, are compatible with alcohol or hydrocarbon solvents only. Accordingly, there is a need for water-based hair spray fixatives which can be formulated into hair spray compositions which can meet VOC regulations. Preferably it is desired to provide new and effective hair spray polymers or fixatives which can be prepared in aqueous medium, and thus can be formulated directly into water-based hair spray compositions which meet VOC requirements. Another object of the invention is to provide such compositions which exhibit good fixative properties, including effective substantivity, conditioning, hold and curl retention properties for the user.

Vinyl caprolactam (VCL)-vinyl pyrrolidone (VP)-dimethylaminoethyl methacrylate (DMAEMA) terpolymers are disclosed in U.S. Pat. No. 4,521,404 and are marketed under the trademark GAFFIX ® resins as a 35-40% solids suspension in ethanol. Attempts to prepare aqueous suspensions of the terpolymer have proven unfeasible due to the relatively low cloud points of these terpolymers; and gradual ethanol-water exchange have proved tedious and uneconomical. Furthermore, such resinous suspensions in a hydroalcohol medium require the addition of thickening agents for gel and paste formulations.

Accordingly, it is an object of this invention to provide polymer hair fixatives of VCL-VP-DMAEMA terpolymers which includes acrylic acid, a process for preparing such polymers in an aqueous or aqueous-alcoholic solvent, wherein the viscosity of the polymer product can be controlled in a predetermined manner, and in which the compositional ranges of monomers in the terpolymer will provide useful fixatives for aqueous-based hair spray compositions.

These and other objects and features of the invention will be made apparent from the following description thereof.

SUMMARY OF THE INVENTION

The present invention provides a polymer hair fixative comprising 5-80% vinyl caprolactam (VCL), 25-90% vinyl pyrrolidone (VP), 2-15% dimethylaminoethyl methacrylate (DMAEMA) and 0.1-5% acrylic acid (AA), in the form of sodium acrylate, by weight of the polymer. These polymers are made by an aqueous-based solution process, particularly in water or water-alcohol solvent to predetermine the viscosity of the product, and water-based hair spray compositions which meet VOC regulations.

DETAILED DESCRIPTION OF THE INVENTION

The polymer hair fixatives of the present invention suitably comprise about 5-80%, preferably 10 to 70%, by weight of vinyl caprolactam, about 25-90%, preferably 35 to 80%, by weight of vinyl pyrrolidone, about 2-15%, preferably 3 to 10%, by weight of dimethylaminoethyl methacrylate and 0.1-5%, preferably 0.5-2.% by weight of acrylic acid, in the form of the acrylate salt, e.g. sodium acrylate.

The polymers of the invention are conveniently prepared in an aqueous or aqueous-alcoholic solution, by subjecting the above monomers, either in admixture, or while being added sequentially into a reactor, to a temperature of about 40° to 120° C., preferably 60 to 80° C., and most preferably 65° C., under agitation in an inert atmosphere, for a period of about 0.5 to 12 hours, preferably 5-10 hours, and most preferably 8 hours, in the presence of about 0.1-5% by weight based on total monomers of a free radical polymerization initiator or catalyst. Representative catalysts include low and high temperature organic and inorganic catalysts, such as peroxides, e.g. hydrogen peroxide; peroxy compounds such as t-butylperoxy pivalate, e.g. Lupersol 11, t-butylperoxy benzoate; and azo compounds, e.g. azobisisobutyronitrile, 2,2'-azobis-(2,4-dimethyl valeronitrile); although other initiators known in the art may be used as well.

The polymerization may be a run in 100% water solvent, or in mixtures of water and alcohol, e.g. isopropanol or ethanol, to provide polymer have specific viscosities of about 0.2-5, preferably about 0.5-2 and most preferably about 1.0. In 100% water, the specific viscosity of the polymer obtained is about 1.5 to 3.5, whereas in water-alcohol mixtures, the specific viscosities produced were about 0.3-1.5, generally about 0.4-1.2.

In water-alcohol mixtures, the reaction product can be stripped of alcohol to provide an all water composition.

The polymerization is run at a solids contents (of monomers) of about 1.0-40%, preferably 15-30%, and most preferably about 20%.

The residual VP content of the product is less than 0.1%, preferably less than 0.05% and most preferably 0%.

Ordinarily the aqueous or aqueous-alcoholic solutions of the polymers thus-obtained are used as such for preparing water-based hair spray compositions which meet VOC regulations; however, if desired, the polymer product itself may be separated from the solution and recovered, for example, by evaporation of solvent, or by other conventional method.

The invention will now be described with reference to the following examples.

EXAMPLES 1-12

PREPARATION OF VCL/VP/DMAEMA/AA POLYMERS IN AQUEOUS-BASED SOLUTION

A one-liter glass resin kettle, fitted with an anchor agitator, a temperature controller, a nitrogen inlet, a monomer feed tube and a condenser, was charged with VCL and distilled water. The solution in the kettle then was purged with nitrogen for 30 minutes with the dip tube was positioned at the bottom of the reactor. The nitrogen flow was continued and the dip tube was raised above the solution. The solution then was heated to 65° C. and a feed of VP/DMAEMA monomers and sodium acrylate were pumped into the kettle at a rate such that the feeds were completed in 2 hours. The start of addition of the feed was considered to be time zero. A first initiator charge of Lupersol 11 was added at time 10 minutes, a second shot of the same amount at 60 minutes, and the remaining third at the completion of the monomer feed. The total addition took approximately 120 minutes whereafter 0.8 g. of initiator had been added. The reaction mixture then was held at 65° C. for an additional 3 hours, heated to 90° C. and 1 g. of t-butyl peroctoate (Triganox 21) was added as an additional initiator. The reaction mixture was maintained at 90° C. for 8 hours, cooled and discharged.

The several VCL/VP/DMAEMA/AA polymers produced according to this general method are summarized in Table I below.

In the examples where an aqueous-alcoholic solvent was used, the alcohol was stripped off to provide an all water product.

TABLE I

PREPARATION OF VCL/VP/DMAEMA/AA POLYMERS IN AQUEOUS-BASED SOLUTION

| EX. NO. | VCL (g) | VP (g) | DMAEMA (g) | AA* (g) | SOLVENT | PRODUCT |
|---|---|---|---|---|---|---|
| 1 | 10 | 85 | 5 | 1 | W-100 | Clear |
| 2 | 10 | 85 | 5 | 1 | W-50 I-50 | Clear |
| 3 | 10 | 85 | 5 | 1 | W-90 I-10 | Clear |
| 4 | 10 | 85 | 5 | 1 | W-75 I-25 | Clear |
| 5 | 10 | 85 | 5 | 1 | W-50 E-50 | Clear |
| 6 | 10 | 85 | 5 | 2 | W-100 | Clear |
| 7 | 20 | 75 | 5 | 1 | W-50 I-50 | Clear |
| 8 | 30 | 65 | 5 | 1 | W-50 I-50 | Clear |
| 9 | 40 | 55 | 5 | 1 | W-50 I-50 | Clear |
| 10 | 50 | 45 | 5 | 1 | W-50 I-50 | Clear |
| 11 | 60 | 35 | 5 | 1 | W-50 I-50 | Clear |
| 12 | 70 | 25 | 5 | 1 | W-50 I-50 | Clear |

*as sodium acrylate

The properties of the aqueous-based solutions of the VCL/VP/DMAEMA/AA polymers produced above are presented in Table II below.

TABLE II

CHARACTERIZATION OF AQUEOUS AND AQUEOUS-ALCOHOLIC SOLUTIONS OF VCL/VP/DMAEMA/AA POLYMERS

| EX. NO. | % SOLIDS | SPECIFIC VISCOSITY | % RESIDUAL VP |
|---|---|---|---|
| 1 | 18.52 | 2.65 | 0.07 |
| 2 | 36.73 | 0.55 | 0.11 |
| 3 | 20.52 | 1.16 | 0.18 |
| 4 | 20.20 | 0.58 | 0.10 |
| 5 | 20.32 | 0.67 | 0.03 |
| 6 | 18.83 | 2.34 | 0.08 |
| 7 | 19.71 | 0.47 | 0.06 |
| 8 | 29.60 | 0.33 | 0.10 |
| 9 | 19.60 | 0.42 | 0.09 |
| 10 | 19.60 | 0.36 | 0.10 |
| 11 | 22.15 | 0.35 | 0.08 |
| 12 | 20.02 | 0.39 | 0.09 |

The water-based hair spray compositions of the invention containing the polymer hair fixative of VCL/VP/DMAEMA/AA suitably comprises about 2 to 20%, preferably 3 to 6%, by weight of the polymer, about 10 to 60%, preferably 15 to 50%, by weight of water, about 20 to 40%, preferably 30 to 35%, by weight of dimethyl ether, and 0 to 15%, preferably 0 to 10%, by weight of ethanol. Such compositions are one-phase systems, can be made directly from the polymer solutions prepared by the aqueous solution process, meet VOC standards, and exhibit excellent performance characteristics in use as a hair spray.

While the mechanism of synergistic action of the four components of the polymer of the invention is not completely understood at present, it is believed that the presence of the VCL monomer therein provides a hydrophobic component which enhances the humidity resistance and hold of the hair spray composition, and the acrylic acid component, in the form of sodium acrylate, further enhances the water solubility of the product, thus providing better removability after use.

EXAMPLE 13

PREPARATION AND EVALUATION OF WATER-BASED HAIR SPRAY COMPOSITIONS

The following water-based hair spray formulations was prepared:

| | |
|---|---|
| Polymer solution, 20% solids (Ex. 2) | 10 g. |
| Water-distilled | 45 |
| Ethanol-anhydrous | 10 |
| Dimethyl ether | 35 |
| | 100 g. |

The formulation was tested in the conventional manner for hold (curl retention at 90% RH and 80° F.) showed 85% average % curl retention after 90 minutes of treatment.

EXAMPLE 14

| | |
|---|---|
| Polymer solution (Exs. 2, 3 or 4) | 10 g. |
| Water-distilled | 55 |
| Dimethyl ether | 35 |
| | 100 g. |

These compositions showed a 70% curl retention after 90 minutes.

While the invention has been described with particular reference to certain embodiments thereof, it will be understood that changes and modifications may be made which are within the skill of the art. Accordingly, it is intended to be bound only by the following claims, in which:

What is claimed is:

1. A hair fixative which is a polymer consisting essentially of about 5 to about 80% by weight vinyl caprolactam, about 25 to about 90% by weight vinyl pyrrolidone, about 2 to about 15% by weight dimethylaminoethyl methacrylate, and about 0.1 to about 5% by weight of sodium acrylate.

2. A hair fixative according to claim 1 with about 10 to 70% by weight vinyl caprolactam, about 35 to 80% by weight vinyl pyrrolidone, about 3 to about 10% by weight dimethylaminoethyl methacrylate, and about 0.5 to about 2% of sodium acrylate.

3. An aqueous or aqueous-alcoholic solution of the polymer of claim 1 having a solids content of about 10 to 40%, a specific viscosity of about 0.2 to 5, and a residual vinyl pyrrolidone level of less than about 0.1%.

4. An aqueous or aqueous-alcoholic solution of the polymer of claim 1 having a solids content of about 15 to 30%, a specific viscosity of about 0.5 to 2, and a residual vinyl pyrrolidone level of less than about 0.05%.

5. An aqueous or aqueous-alcoholic solution according to claim 4 having a solids content of about 20% and a specific viscosity of about 1.0.

6. A solution process which comprises polymerizing 5 to 80% by weight caprolactam, 25 to 90% by weight vinyl pyrrolidone, 2 to 15% bay weight dimethylaminoethyl methacrylate and 0.1 to 5% by weight sodium acrylate in aqueous or aqueous-alcoholic solution at a temperature of about 40° to 120° C., under agitation, in an inert atmosphere, for a period of about 0.5 to 12 hours, in the presence of about 0.1 to 5% based on total monomers of a free radical polymerization initiator, at a 10-40% solids level.

7. A process according to claim 6 wherein said process is carried out in aqueous solution.

8. A process according to claim 6 wherein said process is carried out in an aqueous-alcoholic solution.

9. A process according to claim 6 which is run at about 60°-80° C., for 5-10 hours, with 0.5-1.5% initiator, and at a 15-30% solids level.

10. A process according to claim 6 in which the polymers obtained have a specific viscosity of 0.2-5.

11. A process according to claim 10 wherein said specific viscosity is about 1.5-3.5.

12. A process according to claim 10 wherein said specific viscosity is about 0.3-1.5.

13. A water-based hair spray composition which meets VOC standards comprising about 2 to 10% by weight of the hair fixative of claim 1, about 10 to 60% by weight of water, about 20 to 40% by weight of dimethyl ether, and about 0 to 15% by weight of ethanol.

14. A water-based hair spray composition according to claim 13 which comprises about 3 to 6% by weight of the hair fixative of claim 1, about 15 to 50% by weight of water, about 30 to 35% by weight of dimethyl ether, and about 0 to 10% by weight of ethanol.

15. A water-based hair spray composition according to claim 13 in which the hair fixative has the composition of claim 2.

16. A water-based hair spray composition according to claim 13 which exhibits an average % curl retention of at least 70% after 90 minutes of treatment at 90% RH and 80% F.

* * * * *